(12) United States Patent
Sablone et al.

(10) Patent No.: US 10,231,884 B2
(45) Date of Patent: Mar. 19, 2019

(54) METHOD AND A MACHINE FOR PRODUCING ABSORBENT SANITARY ARTICLES AND CORRESPONDING ABSORBENT SANITARY ARTICLE

(71) Applicant: Fameccanica.Data S.p.A., Pescara (IT)

(72) Inventors: Gabriele Sablone, Montesilvano (IT); Franco Silveri, Sambuceto di San Giovanni Teatino-Chieti (IT); Giuseppe Pagliarella, Pescara (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 114 days.

(21) Appl. No.: 15/292,398

(22) Filed: Oct. 13, 2016

(65) Prior Publication Data

US 2017/0105882 A1 Apr. 20, 2017

(30) Foreign Application Priority Data

Oct. 15, 2015 (IT) .................. 102015000061931

(51) Int. Cl.
*A61F 13/15* (2006.01)

(52) U.S. Cl.
CPC .. *A61F 13/15804* (2013.01); *A61F 13/15658* (2013.01); *A61F 13/15723* (2013.01);
(Continued)

(58) Field of Classification Search
CPC .......... A61F 13/15577; A61F 13/15585; A61F 13/15699; A61F 13/15723;
(Continued)

(56) References Cited

U.S. PATENT DOCUMENTS 7,500,941 B2 3/2009 Coe et al.
2012/0061015 A1 3/2012 Lavon et al.
(Continued)

FOREIGN PATENT DOCUMENTS

EP 0263720 A1 4/1988
EP 0295957 A1 12/1988
(Continued)

OTHER PUBLICATIONS

Italian Search Report and Written Opinion dated Jun. 24, 2016 for Application No. UB20154695.

*Primary Examiner* — John L Goff, II
(74) *Attorney, Agent, or Firm* — Patterson + Sheridan, LLP

(57) ABSTRACT

A method and a machine for producing absorbent sanitary articles comprising a central body and pairs of front and rear side panels. The side panels are obtained from two continuous web materials on which a series of first transverse cuts are carried out, alternating with a series of second transverse cuts, defining on each of said web materials a first and a second succession of front and rear side panels in which each of the front panels is preceded and followed by one of the rear panels, and each of the rear panels is preceded and followed by one of the front panels, and wherein the proximal edge of each of the rear panels is aligned with the distal edge of each of the front panels and the distal edge of each of the rear panels is aligned with the proximal edge of each of the front panels.

13 Claims, 11 Drawing Sheets

(52) U.S. Cl.
CPC .. *A61F 13/15739* (2013.01); *A61F 13/15764* (2013.01); *A61F 2013/15821* (2013.01)

(58) Field of Classification Search
CPC .......... A61F 13/15739; A61F 13/15747; A61F 13/15756; A61F 13/15764; A61F 13/15804; B32B 37/18; B32B 37/182; B32B 37/185; B32B 37/187; B32B 37/22; B32B 37/223; B32B 37/226; B32B 38/0004; B32B 38/1808; B32B 38/185; B29C 65/7802; B29C 65/782; B29C 65/7861

See application file for complete search history.

(56) References Cited

U.S. PATENT DOCUMENTS

| | | | |
|---|---|---|---|
| 2013/0035222 | A1 | 2/2013 | Andrews et al. |
| 2014/0018222 | A1* | 1/2014 | Sablone ............ A61F 13/15756 493/374 |
| 2015/0202091 | A1* | 7/2015 | Sablone ............ A61F 13/15585 156/308.2 |
| 2017/0326005 | A1* | 11/2017 | Piantoni ............ A61F 13/15577 |

FOREIGN PATENT DOCUMENTS

| | | |
|---|---|---|
| EP | 1179495 A1 | 2/2002 |
| EP | 1772403 A1 | 4/2007 |
| WO | 0191666 A2 | 12/2001 |

* cited by examiner

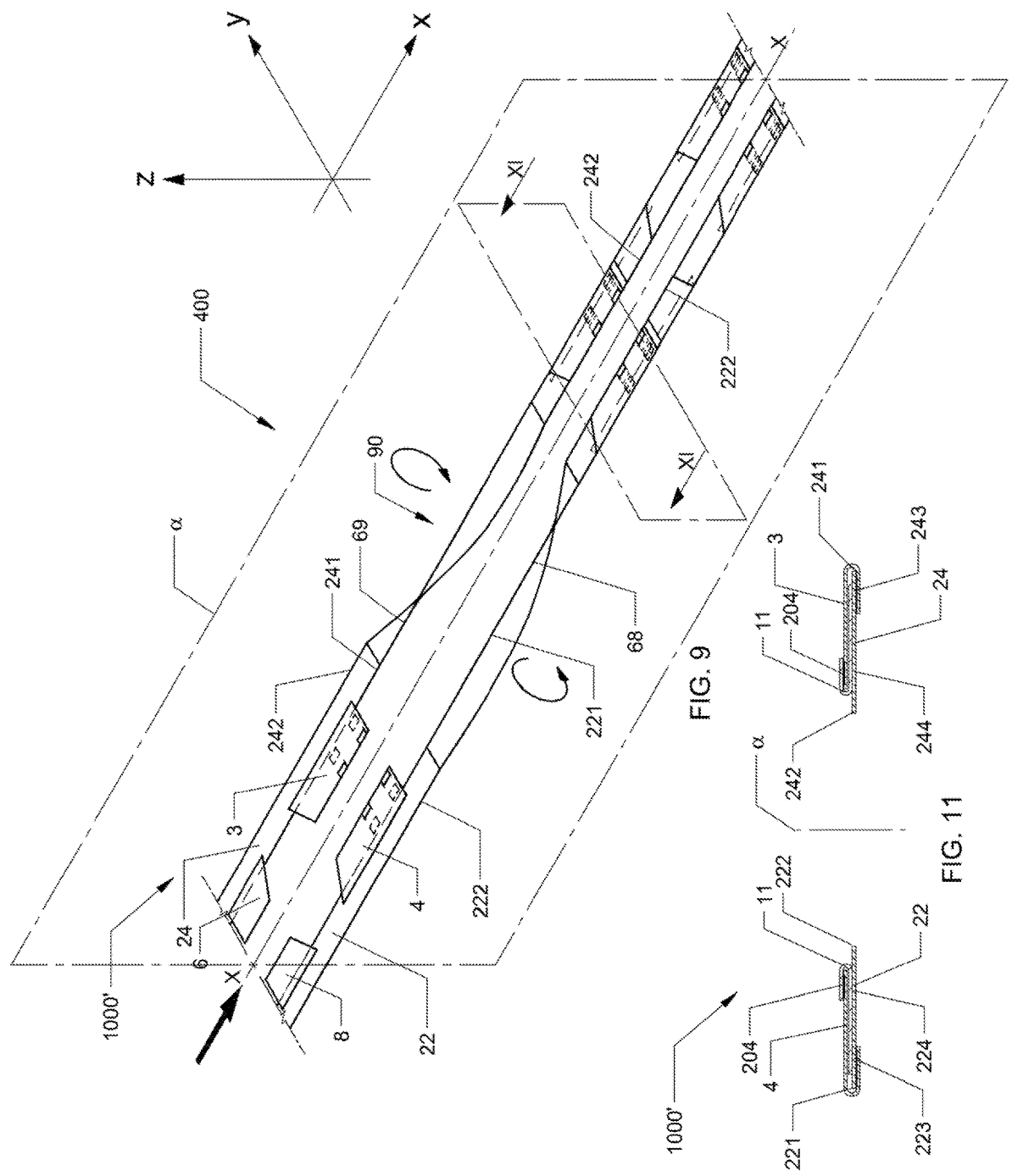

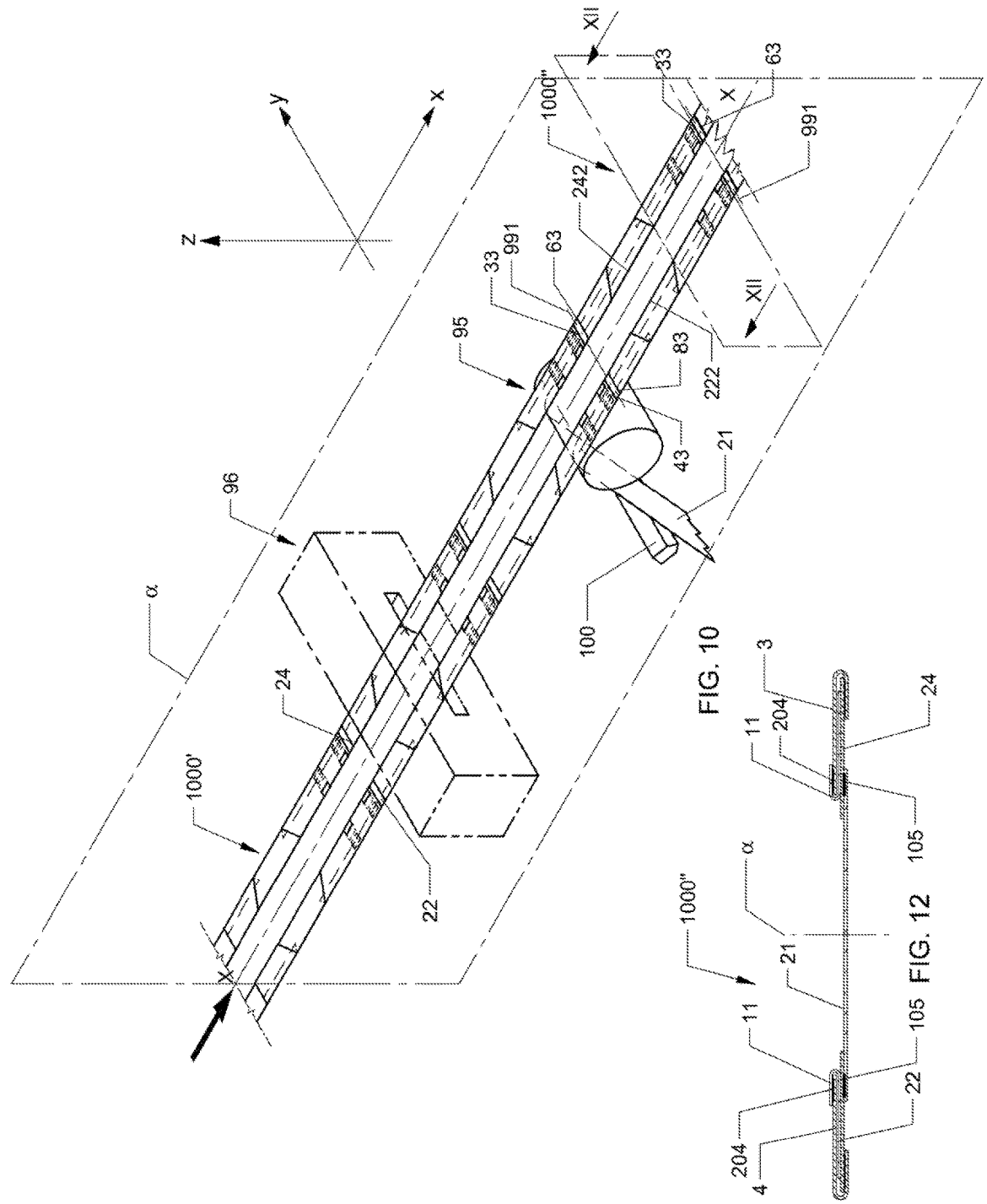

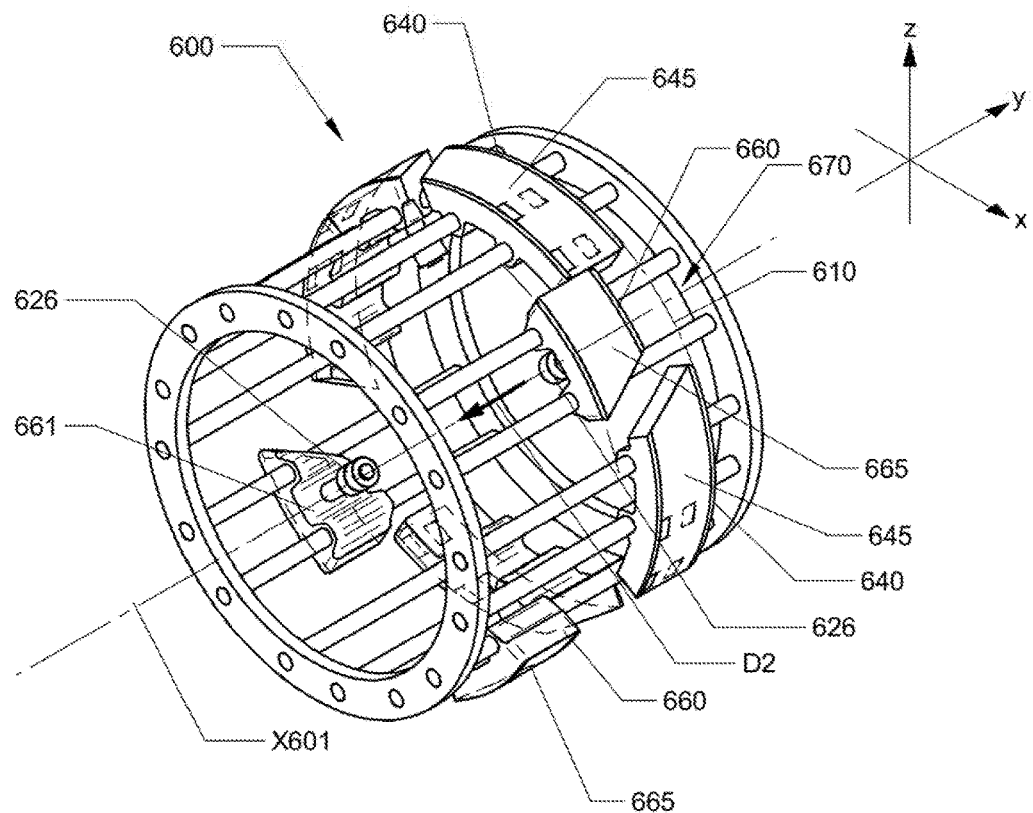
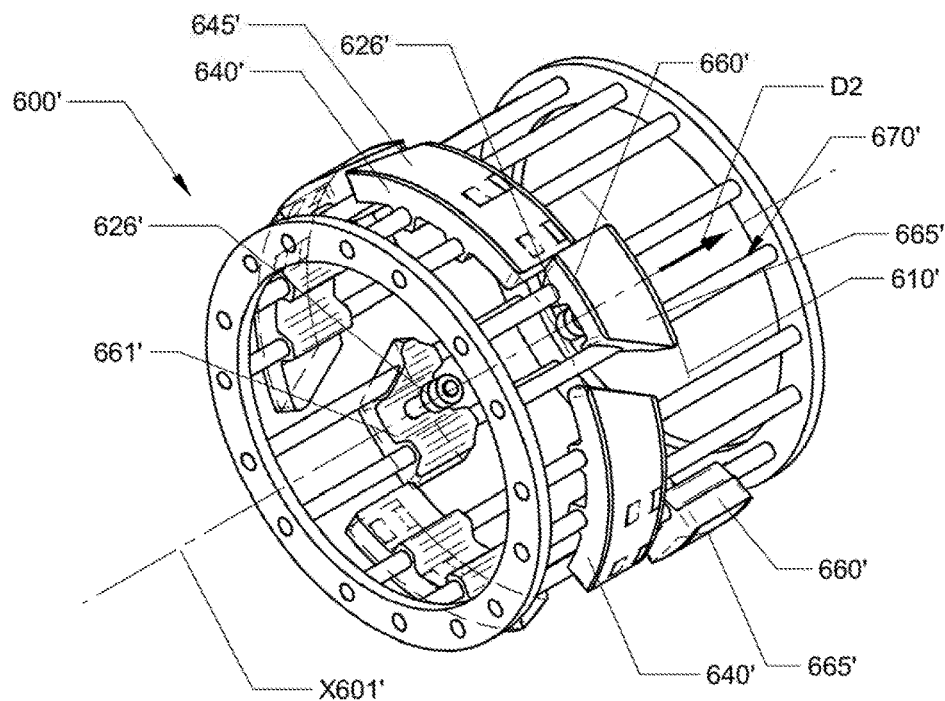
FIG. 14

METHOD AND A MACHINE FOR PRODUCING ABSORBENT SANITARY ARTICLES AND CORRESPONDING ABSORBENT SANITARY ARTICLE

CROSS-REFERENCE TO RELATED APPLICATIONS

This application claims benefit of Italian patent application number 102015000061931, filed Oct. 15, 2015, which is herein incorporated by reference.

BACKGROUND OF THE INVENTION

Field of the Invention

The present description regards a method and a machine for producing absorbent sanitary articles.

In particular, the present invention is preferably used for producing absorbent sanitary articles, such as, for example, diapers for children and/or incontinence pads for adults, comprising a central body and two pairs of side panels connected to the ends of the central body.

Description of Prior Art

In the field of absorbent sanitary articles, the market requires machines and manufacturing methods able to produce absorbent articles that comprise:

a central body provided with an absorbent element, which can be placed around the user's crotch region, which extends in the longitudinal direction between a first waist end or rear end and a second waist end or front end, opposite to each other, a first pair of side panels or rear panels connected to the first waist end or rear end of the central body and able to define, at least in part, the waist end of the article; and a second pair of side panels or front panels connected to the second waist end or front end of the central body and able to define, at least in part, the waistband of the article.

The aforesaid machines, and their manufacturing methods, must ensure an optimal management of the processes of manipulating and applying the side panels, in particular for absorbent articles intended for incontinent adults. In this case, absorbent articles are involved that can have a total length and width of about one meter, or rather, dimensions such as to enable the individual absorbent article to achieve circumferences in the order of 200 cm.

It is evident that for absorbent products of these dimensions, the operations of forming and applying the side panels on the central body of the sanitary article are critical, and these operations are made even more difficult by the very high production rates, in the order of hundreds of absorbent articles per minute (typically 300-400 absorbent articles per minute).

To the above it should be added that a further fundamental requirement for sanitary articles intended for incontinent users is to have the side panels with the ends forming the openings of the legs shaped so as to confer a classic hourglass configuration to the absorbent article.

The conventional methods for producing shaped panels imply that the conformation of the shape is created by removing part of the material of the panels themselves, thereby generating waste that would negatively affect the cost of the absorbent article.

The requirements outlined above highlight two problems:

applying the side panels on individual absorbent products with a simple method and that can eliminate the folding operations of the side panels on the central body of the sanitary article; and providing shaped side panels, which can be formed without generating waste of material.

SUMMARY OF THE INVENTION

The object of the present invention is that of providing a method for producing absorbent sanitary articles that resolves the abovementioned problems.

Furthermore, the object of this invention is to provide a compact and efficient machine for producing absorbent sanitary articles.

The invention also regards a corresponding absorbent sanitary article produced with the present method.

The claims form an integral part of the disclosure provided here in relation to the invention.

BRIEF DESCRIPTION OF THE DRAWINGS

The invention will now be described, purely by way of non-limiting example, with reference to the attached drawings, in which:

FIG. 6 to FIG. 10 are schematic perspective views of a method for producing and applying the side panels according to a preferred embodiment.

FIG. 11 is a cross-section along the line XI-XI of FIG. 9.

FIG. 12 is a cross-section in the plane XII-XII of FIG. 10.

FIG. 14 is a perspective view of an apparatus used in a preferred embodiment of the method.

DETAILED DESCRIPTION

In the following description various specific details are illustrated aimed at a thorough understanding of the embodiments. The embodiments may be implemented without one or more of the specific details, or with other methods, components, materials, etc. In other cases, known structures, materials or operations are not shown or described in detail to avoid obscuring various aspects of the embodiments.

The reference to "an embodiment" in the context of this description indicates that a particular configuration, structure or characteristic described in relation to the embodiment is included in at least one embodiment. Therefore, phrases such as "in an embodiment", possibly present in different places of this description do not necessarily refer to the same embodiment. Moreover, particular configurations, structures or characteristics can be combined in any convenient way in one or more embodiments.

The references used here are only for convenience and do not therefore define the field of protection or the scope of the embodiments.

Two elements are considered here to be connected together when they are permanently joined directly or indirectly, such as in the case in which each element is directly connected to intermediate elements.

Furthermore, the connotations "front" and "rear" are used here only to distinguish the relative position of elements such as, for example, the two pairs of side panels, without this being intended in a limiting sense of the ways in which the absorbent sanitary article is worn.

Figure 1:
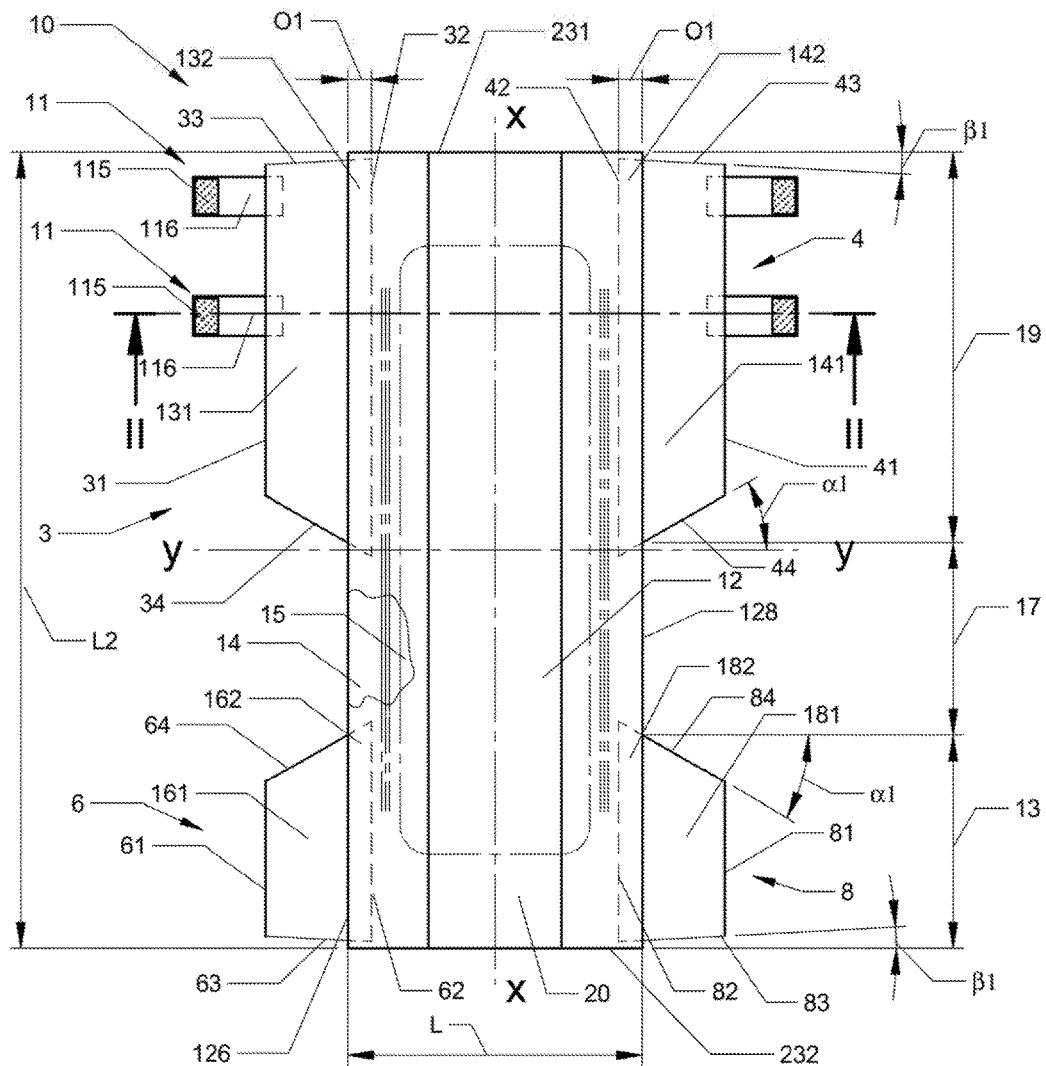
FIG. 1 is a plan view of an absorbent sanitary article provided with side panels of the type described here, represented in the extended position.

In FIG. 1, the reference number 10 indicates the whole of an absorbent sanitary article of conventional type, intended to be sold opened and to be closed only after being placed on the wearer's body. By way of reference, and without any intention of limiting the possible field of application, the absorbent sanitary article 10 can be an absorbent article for incontinent adults.

The absorbent sanitary article 10 is depicted in FIG. 1 in the unfolded and extended condition in plan view and, according to a general configuration known per se, it comprises a central body 12 intended to be applied around the user's crotch area according to a general basin or U-shape conformation. The main body 12 comprises:

a first composite material in sheet form or "topsheet" 20, typically permeable to liquids and intended to be facing towards the user's body;

a second material in sheet form or "backsheet" 14 typically impermeable to body fluids and intended to be facing outwards, or rather in contact with the clothing worn by the user; and an absorbent structure or "core" 15 interposed between the topsheet 20 and the backsheet 14.

On the central body 12, it is possible to identify: a first waist (or rear) region 19, a second waist (or front) region 13, and a crotch region 17 interposed between the front and rear waist regions 19, 13.

Furthermore, on the central body 12, it is possible to identify a longitudinal axis X-X and a transverse axis Y-Y, perpendicular to each other, as well as a first side edge 126 and a second side edge 128, typically parallel to the longitudinal axis X-X, which define the width L of the central body 12 and a first waist (or rear) edge 231 and a second waist (or front) edge 232 parallel to the transverse axis Y-Y.

Figure 2:
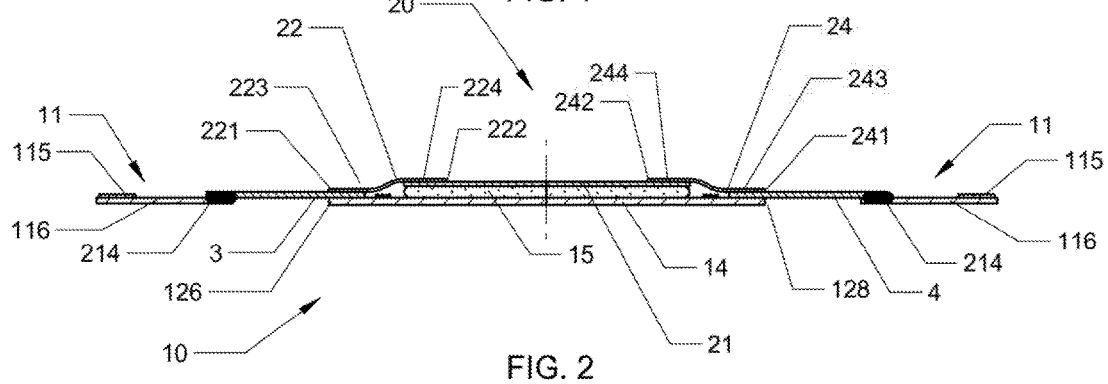
FIG. 2 is a cross-section along the line II-II of FIG. 1.

In the preferred embodiment described below, as represented in FIG. 2, the first composite material in sheet form or "topsheet" 20 is a sheet material made by placing together three separate sheet materials:

a central web material 21, typically permeable to body fluids; and a first and a second side sheet (or web material) 22 and 24.

On the first side web material 22, it is possible to identify:

an outer edge 221;

an inner edge 222;

a first end region 223 adjacent to the outer edge 221; and a second end region 224 adjacent to the inner edge 222.

Similarly, on the second side web material 24, it is possible to identify:

an outer edge 241;

an inner edge 242;

a first end region 243 adjacent to the outer edge 241; and a second end region 244 adjacent to the inner edge 242.

As shown in FIG. 1, the central body 12 is typically rectangular.

In the absorbent sanitary article 10, shown in FIGS. 1 and 2, the outer edges 221 and 241, respectively, of the first and second side web materials 22 and 24, face outwards and typically coincide with the corresponding side edges 126 and 128 of the central body 12. Consequently, the inner edges 222 and 242 of the side web materials 22 and 24 face towards the longitudinal axis X-X of the absorbent sanitary article 10.

In further examples of embodiments, not illustrated, the end regions 224 and 244 next to the inner edges 222 and 242 may be unattached to the web material 21 and can be provided with elastic elements which, when the absorbent product 10 is shaped in basin-form to be worn, contribute to lift up the aforesaid end regions, forming side barriers to possible fluid leakages. Further improvements to the effect of liquid containment can be implemented by choosing materials with hydrophobic characteristics for the side sheets 22 and 24.

The side web materials 22 and 24 with the second elasticized end regions 224 and 244 can be made with various methodologies and structures. In the patent literature there are several examples of side webs or cuffs suitable for this purpose, by way of example see EP-A-0263720 "Absorbent article having leakage resistant dual cuffs".

The materials for producing the sheets necessary for forming the topsheet 20 can be chosen from natural or synthetic fibers, such as cotton, polyester or polypropylene fibers; they can also be a mixture of synthetic and natural fibers.

A suitable material for producing the central sheet 21 permeable to the liquids of the topsheet 20 is a non-woven fabric of 25 $g/m^2$ of polypropylene fibers made with Spunbond technology, made hydrophilic by a surface treatment with surfactant products such as Ahcovel N-62 by the Hodgson Textile Chemicals of Mount Holly, N.C. U.S.A. and/or Glucopan 220UP from the Henkel Corporation of Amber, Pa. U.S.A.

A suitable material for producing the side web materials 22 and 24 can be a non-woven fabric of 20 $g/m^2$ of polypropylene fibers produced with SMS (Spunbond Meltblown Spunbond) technology.

In the preferred embodiment of FIG. 1, the first waist region 19 is typically provided with a pair of panels formed by a first rear side panel 3 and a second rear side panel 4, which extend laterally outwards from the central body 12.

Similarly, the second waist region 13 is provided with a pair of front side panels formed by a first front side panel 6 and a second front side panel 8, which extend laterally outwards from the central body 12.

On the first rear side panel 3 it is possible to identify:

a distal edge 31;

a first end (or distal) region 131 adjacent to the distal edge 31;

a proximal edge 32;

a second end (or proximal) region 132 adjacent to the proximal edge 32;

an outer edge 33; and an inner edge 34.

The second rear side panel 4 similarly defines:

a distal edge 41;

a first end (or distal) region 141 adjacent to the distal edge 41;

a proximal edge 42;

a second end (or proximal) region 142 adjacent to the proximal edge 42;

an outer edge 43; and an inner edge 44.

Similarly on the first front side panel 6, it is possible to identify:

a distal edge 61;

a first end (or distal) region 161 adjacent to the distal edge 61;

a proximal edge 62;

a second end (or proximal) region 162 adjacent to the proximal edge 62;

an outer edge 63; and an inner edge 64.

The second front side panel 8 also defines:
a distal edge 81;
a first end (or distal) region 181 adjacent to the distal edge 81;
a proximal edge 82;
a second end (or proximal) region 182 adjacent to the proximal edge 82;
an outer edge 83; and
an inner edge 84.

The first end (or distal) region of each side panel is typically the part of the panel that externally projects from the central body 12, while the second end (or proximal) region is the part of the panel that is connected to the central body 12.

The outer edges 33, 43, 63 and 83 join together the distal and proximal edges of the relative side panel and, in cooperation with the respective waist edge 231, 232 of the central body 12, help to define the waistline of the sanitary article 10.

The inner edges 34, 44, 64 and 84 join together the distal and proximal edges of each panel and complete the perimeter of each panel. Typically, the inner edges 34, 44, 64 and 84 are oblique with respect to the respective distal and proximal edges. Furthermore, the inner edges 34 and 64, in cooperation with the first side edge 126 of the central body 12 and the inner edges 44 and 84, in cooperation with the second side edge 128 of the central body 12, define the contour of the openings for the passage of the legs of the user.

The rear side panels 3 and 4 are typically provided with closure formations 11 at their respective distal edges 31 and 41, which can be of the type with micro-hooks (hook-and-loop) or adhesives, and which allow the closure of the absorbent sanitary article around the user's waist in the standard pant-type configuration.

The closure formations 11 can be produced in various forms and with different combinations of materials, which can give rise to various solutions known in the art.

Typically, as already mentioned, the various closure formations 11 available in the market, are distinguished from each other by the closure means 115, which can be an adhesive element or a component with micro-hooks, and by the supporting element 116, which can be produced with a very varied range of materials, which, in turn, can be either rigid or elastic. In the latter case, the supporting elements 116 are typically transversely stretchable, that is, are elastic along a direction parallel to the transverse axis Y-Y of the sanitary article 10, in order to facilitate the operation of coupling and make it more comfortable to the user that wears it.

In the following description, for simplicity, reference will be made to the closure formations 11 that comprise closure means with micro-hooks 115.

On the sanitary article 10, the closure formations 11 are typically folded inwards relative to the side panels to then be unfolded outwards (as shown in FIG. 1 or in FIG. 2) when the absorbent article is worn by the user so as to connect the micro-hooks (or the adhesive) of the closure means 115 with the outer surface of the front side panels 6, 8 or the outer surface of the front waist region of the central body 12.

Figure 3:
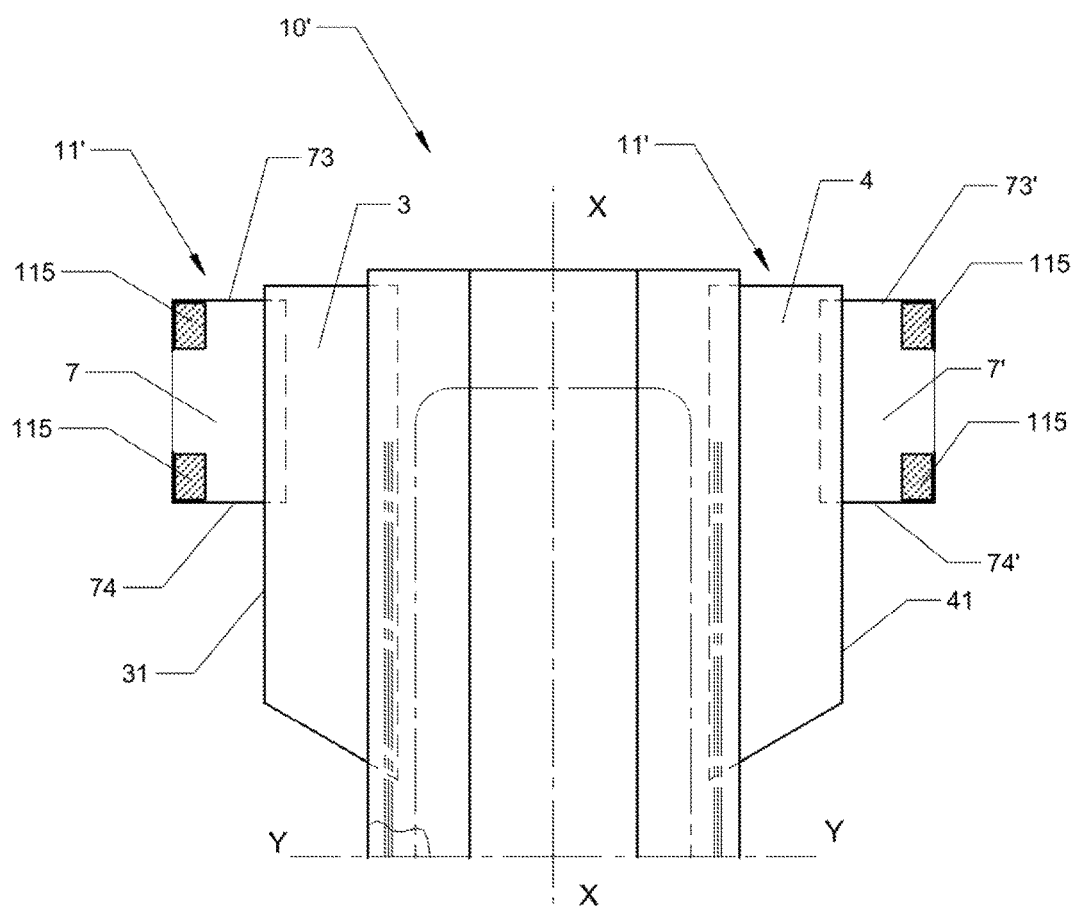
FIG. 3 is a partial plan view of a variant of the sanitary article of FIG. 1.

FIG. 3 illustrates in detail a closure formation 11' that is particularly advantageous for sanitary articles 10' intended for incontinent adults, in which a further panel 7, 7' is connected to each rear side panel 3, 4 at the respective distal edge 31, 41, carrying one or, preferably, more closure means 115 (adhesive formations, or formations with hooks and/or loops, etc.).

Each of the panels 7, 7' can be connected near the distal edge 31, 41 of the respective rear panel 3, 4 using different techniques such as: gluing, thermowelding, ultrasonic welding (possibly used in a combined manner, for example gluing reinforced with thermowelding or ultrasonic welding).

The panels 7, 7' carrying the closure means 115 can be produced with various shapes and with a variety of materials.

Regarding the shape, as shown in FIG. 3, in the absorbent article 10', the panels 7, 7' carrying the closure means 115 have a rectangular shape with pairs of sides perpendicular and parallel to the longitudinal axis X-X of the article 10', respectively.

Regarding the materials, in various embodiments, the panels 7, 7' carrying the closure means 115 can be produced with a non-woven material of current use in the manufacture of sanitary articles, analogous to that used to produce side panels 3, 4, 6 and 8.

In other embodiments, the panels 7, 7' carrying the closure means 115 can have extensibility characteristics of the transverse elastic type, parallel to the longitudinal axis Y-Y, being produced, for example, with the solution described in U.S. Pat. No. 6,572,595 or U.S. Pat. No. 6,994,761, so as to also demonstrate characteristics of "breathability".

It should be noted that the panels 3, 4, 6 and 8 are intended to be applied to pairs of "twin" elements at the opposite sides of the main body 12 in conditions of specular symmetry with respect to the longitudinal axis X-X of the article 10. Each of the rear panels 3, 4 and the front panels 6, 8 typically has a tapered shape, which approximates to the shape of a trapezoid in which the proximal edge constitutes the larger base, while the distal edge forms the smaller base.

In the embodiment considered here, shown in FIG. 1, each inner side 34, 44, 64, 84 of each side panel, both rear and front, form an angle α1 with respect to a direction orthogonal to the axis X-X, similarly each outer side 33, 43, 63 and 83 of the side panels form an angle β1. still with respect to a direction orthogonal to the axis X-X.

Therefore, it follows that in the absorbent article 10 of the preferred embodiment illustrated in FIG. 1, the side panels 3, 6, and 4, 8 typically have inner edges 34, 64 and 44, 84 and outer edges 33, 63 and 43, 83 that present a specular symmetry with respect to both the longitudinal axis X-X and the transverse axis Y-Y of the article 10.

To shape the inner side 34, 44, 64, 84 of each side panel, an angle α1 is typically chosen, which has an amplitude between 30° and 70°, still more preferably between 40° and 50°.

A significant feature of the solution described herein lies in the fact that, even if the angles β1 may tend to 0 (zero), as the respective outer edges (33, 63, 43, 83) are perpendicular with respect to the axis X-X, the choice of a value different from 0 (zero) facilitates the production of the side panels, in fact, as is well-known to the skilled person, an inclined cutting profile (even if only slightly, for example 0.5°-2°) increases the duration of the knife.

The side panels 3, 4, 6 and 8 can be produced with materials made according to the criteria better described in the documents WO-A-01/91666 and WO-A-01/92013, or can be webs of non-woven material. Regarding the possibility of conferring characteristics of "breathability" to the panels, there are also the formation of openings that allow the passage of vapor and contribute to keeping the wearer's skin dry. A suitable material for producing the side panels is the non-woven type spunmelt, identified by the code HX0103500 of 35 g/m², produced by Fibertex Personal Care SA, Svendborgvej 2, DK-9220 Aalborg Denmark.

Figure 4:
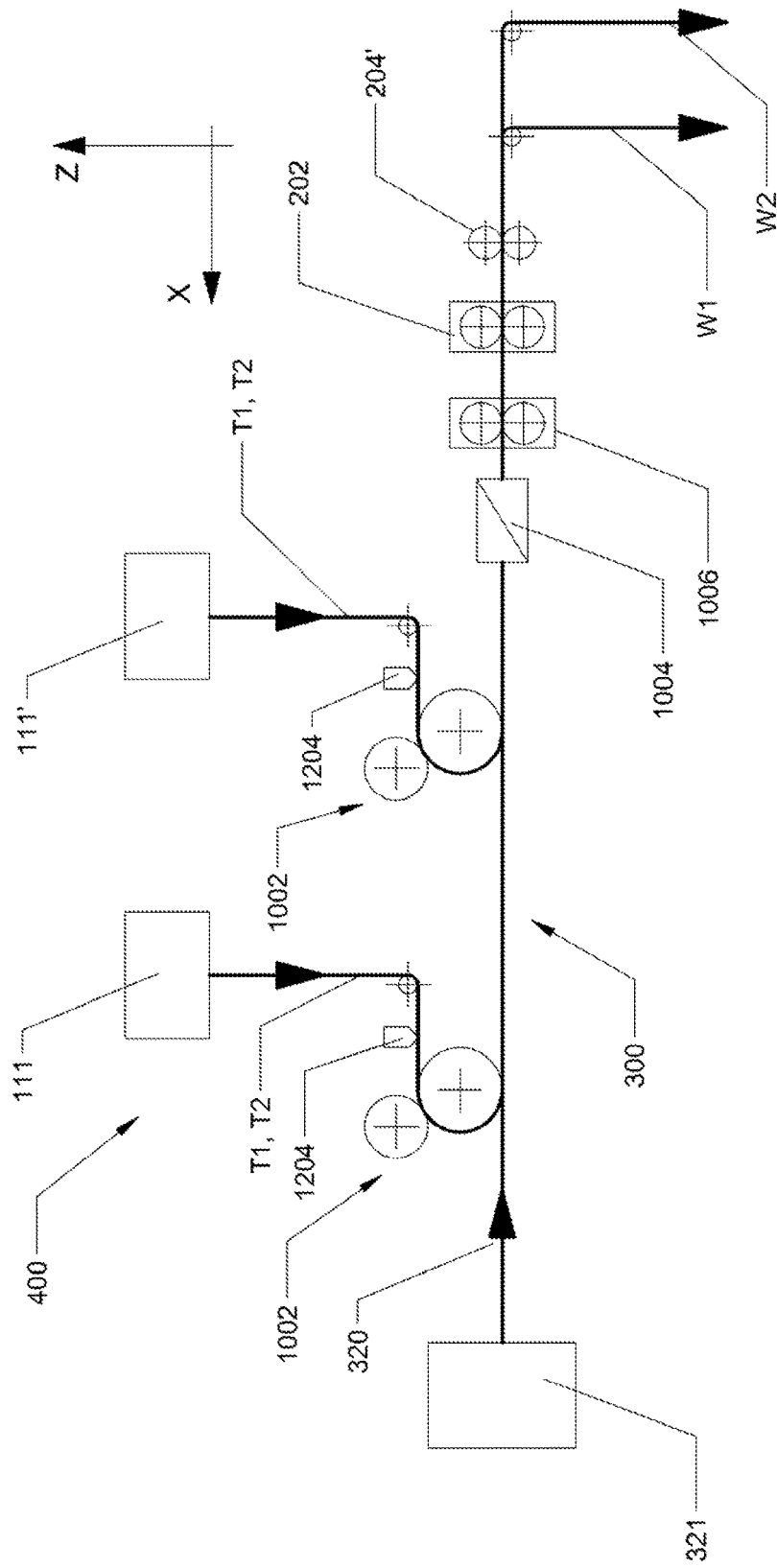
FIGS. 4 and 5 are schematic views of a machine for producing and applying side panels according to a preferred embodiment.
Figure 5:
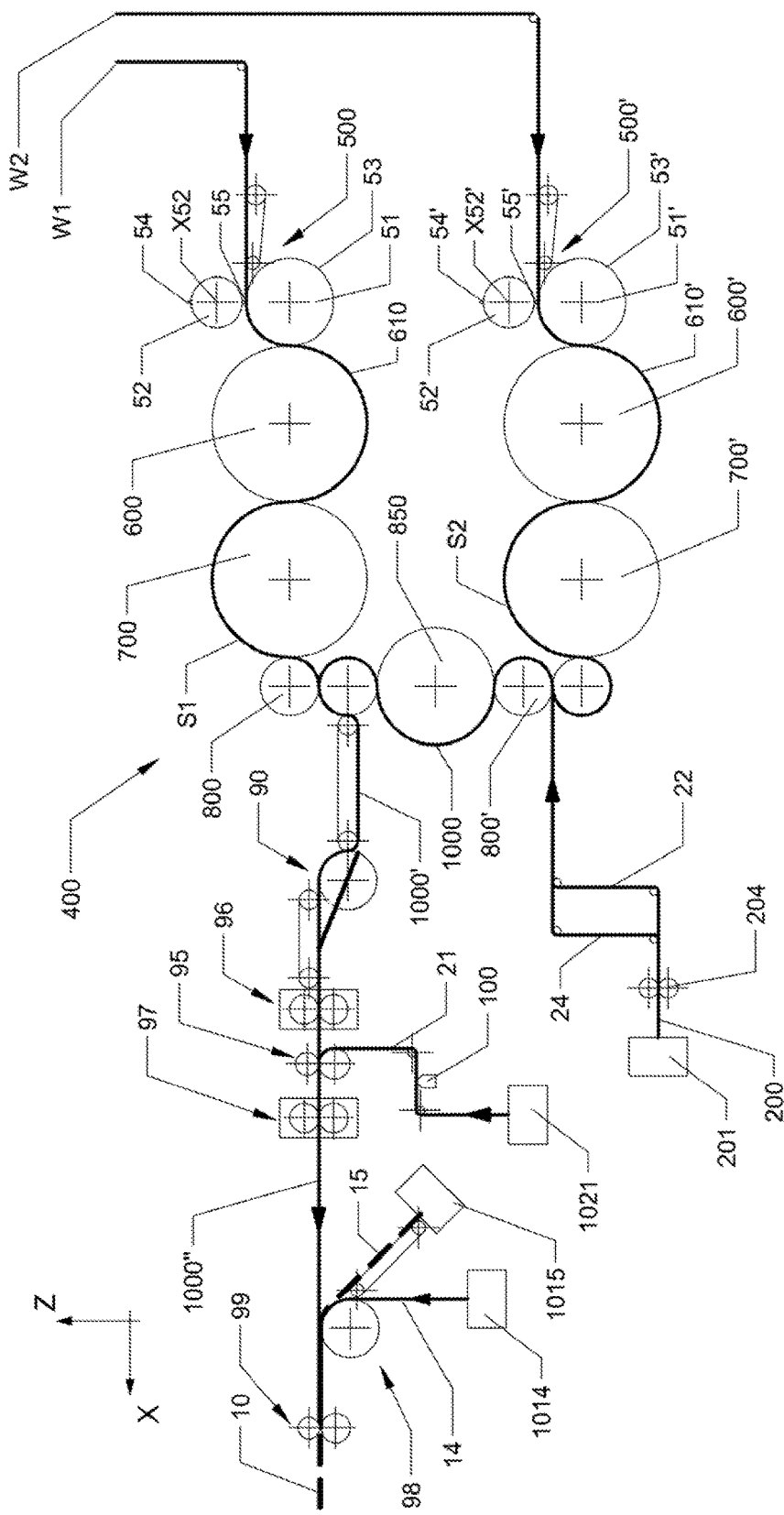

In FIGS. 4 and 5, a machine 400 is schematically illustrated, capable of producing sanitary articles 10 according to a preferred embodiment of the present invention, in which the front and rear side panels 3, 4, 6 and 8 are made from a single web material 320.

To facilitate the understanding of the various steps of the production process, the simplified schematic perspective views of FIGS. 6, 7, 8, 9, 10 and 13 will be used, in which certain operations, which in the preferred embodiment illustrated in FIG. 5, are implemented on rotary drum units; in the aforesaid figures, they are represented as if they were organized in plan form. In addition, in FIG. 13, the operating steps of the method are shown side-by-side rather than overlapping, as will become more evident in the following description.

In the machine 400, it is possible to identify a first main (or longitudinal) direction X, a second main (or transverse) direction Y orthogonal to the first main direction X, and a third main direction Z, orthogonal to both the first main direction X and the second main direction Y. In addition to this, the first main direction X is contained in a vertical centerline plane α of the machine 400. Furthermore, the aforesaid vertical centerline plane α typically contains the longitudinal axis X-X of the precursor blanks of sanitary articles 10.

With reference to FIG. 5, in the preferred embodiment, the machine 400 is typically fed with a web material 200 supplied from a web material unwinding device 201, well-known in the art. The web material 200 is typically advanced through a longitudinal cutting device 204, which is also well-known in the art, which subdivides the web 200 along its axis of symmetry X200 into the first side sheet (or web material) 22 and into the second side sheet (or web material) 24, equal to each other.

The longitudinal cutting operation, as will be seen better below, generates respective outer edges 221 and 241 in the two side web materials 22 and 24, or rather the edges that on the finished product are typically facing outwards, but that immediately after the longitudinal cut and for part of the production method of the machine 400, are left facing each other on opposite faces of the vertical centerline plane α.

Immediately after cutting, the two side web materials 22 and 24 are typically spaced apart transversely, or rather parallelly to the second main direction Y, bringing their outer edges 221 and 241 to a first distance L1, always keeping them equidistant from the vertical centerline plane α.

The first distance L1 to which the two outer edges 221 and 241 are brought, as will be appreciated better in the following description, can be advantageously equal to the width L of the central body 12 of the sanitary article 10.

In the preferred embodiment illustrated in FIG. 4, the machine 400 comprises an application device 300, which is typically fed with a web material 320 supplied from a web material unwinding device 321, well-known in the art, with which with two webs W1 and W2 are produced that are intended to give rise to the front side panels 6, 8 and rear side panels 3, 4, intended to be applied on the central body 12, according to the methods described below.

As illustrated in FIG. 4, in the applicator device 300, the closure formations 11 of the type already described previously (adhesive, micro-hooks, etc.) are applied onto the web 320.

The closure formations 11 can be joined to the web 320 by a suitable application device 1002 (for example of the "cut-and-slip" type), well-known in the art and that, therefore, does not require detailed description herein.

In the preferred embodiment illustrated in FIG. 4, since the sanitary article 10 used as a reference in the present description has two closure formations 11 on each side, two application units 1002 are advantageously present, each of which applies a pair of closure formations 11.

Each of the application units 1002 is typically fed with two tape materials T1 and T2 from which, by the segmentation action implemented by the knives of which the application unit 1002 is equipped, the closure formations 11 are obtained. The tape materials T1 and T2 are typically dispensed by tape material unwinding apparatuses 111 and 111', well-known in the art.

Figure 6:
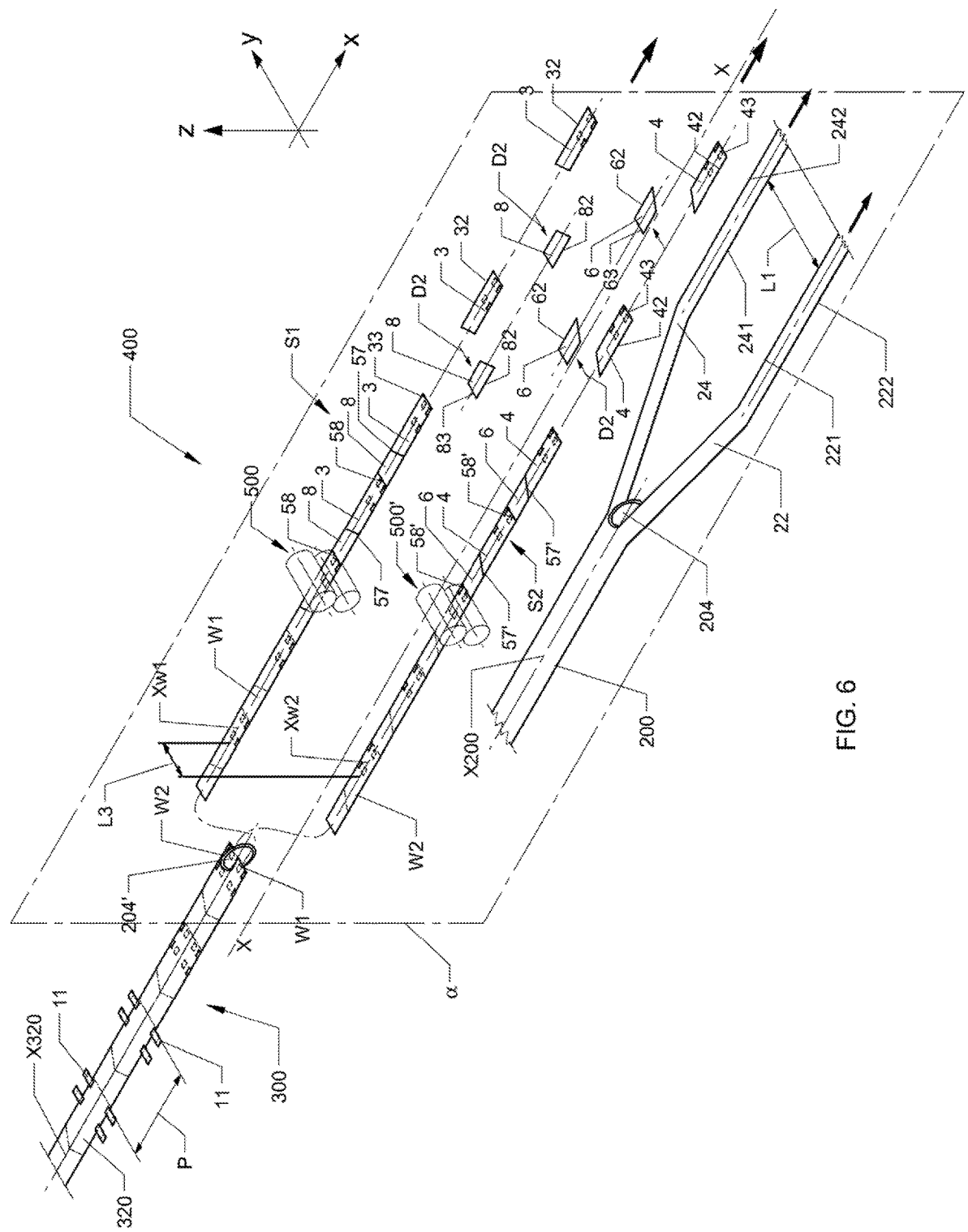

Each of the application units 1002 applies the pairs of closure formations 11 on opposite sides of the web 320 specularly with respect to the longitudinal axis of the web material 320, indicated by X320 in FIG. 6. In other words, the closure formations 11 applied by each application unit 1002 are transversely aligned with each other. Each application unit 1002 applies the respective pairs of closure formations 11 at an application pitch P, as shown in FIG. 6.

The application pitch P of the closure formations 11 typically results as being equal to the sum of the lengths of the distal edge and the proximal edge of a pair of adjacent panels. To facilitate the understanding of the production process, as illustrated in FIG. 6, on the web material 320, the edges of the various front panels 6, 8 and rear panels 3, 4, have been marked with dashed and dotted lines, which are produced with subsequent cutting operations.

With reference to FIGS. 2 and 4, the tapes T1 and T2 can be coated with a layer of adhesive 214 with the adhesive application units 1204, before they are segmented in the application stations 1002. Typically, the adhesive coating 214 is carried out on the tapes T1 and T2 along the respective side bands that come in contact with the regions in the vicinity of the side edges of the web 320 on which the rear side panels 3 and 4 will be identified as the distal regions 131 and 141, respectively.

After attaching the closure formations 11 on the web material 320, it is made to flow through a folding device 1004, known in the art, which completes the application operation by folding them into a general V-shape so as to bring them to embrace the faces opposite the web 320 itself.

It is possible to strengthen the bond of each closure formation 11 with the edges of the web 320 by means of an pressing operation achieved in a pressing station 1006, located downstream of the folding device 1004. The pressing station 1006 is typically provided with a pair of counter-rotating rollers kept pressed against one another with suitable thrust means, such as pneumatic cylinders.

Located downstream of the folding device 1004 and of the pressing station 1006, a further welding unit 202 can be arranged, with the function of producing so-called "temporary" or "technical" welds, between the side end regions of the web 320 and the closure formations 11 folded on the web 320 itself, so that the closure formations 11 in the further production method always maintain the folded configuration. This operation is particularly advantageous in the production of absorbent articles that use closure formations 11' illustrated in FIG. 3.

The characteristic of the "technical" welds is that of being strong enough to prevent the V-shaped closure formations 11 folded on themselves from re-opening during the steps of construction and packaging of the sanitary article 10 and, at the same time, to be sufficiently weak to break during the action of opening or "peeling" exerted by the user, without damage to either the closure formations 11 or the web material 320 that constitutes the rear side panel of the sanitary article 10.

To this end, the welding unit 202 can produce the so-called technical welds, for example, by means of an action of relatively mild thermowelding or ultrasonic welding, or rather through the application of a so-called "always green" glue.

Adhesives able to produce this function of technical welding are known, for example, in the production of the Savaré company of Milan.

With reference to FIGS. 4 and 6, once the operation of applying the closure formations 11 is completed, the web material 320 is passed through a cutting unit 204' (for example, a vertical blade cutter of known type), which cuts the web material 320 along its axis of symmetry X320 and subdivides it into two webs, respectively indicated with W1 and W2, each of which has a respective longitudinal axis Xw1 and Xw2.

As shown in FIG. 6, the longitudinal axes Xw1, Xw2 of the two webs W1 and W2 are typically spaced apart in the transverse direction by a center-to-center distance L3. The webs W1, W2 are crossed with respect to the vertical centerline plane α, so as to reverse them with respect to the upstream position of the cutting device 204'. That is, the edges generated by the longitudinal cutting device 204', which immediately after the cut face opposite each other, after the crossing operation of the two webs W1 and W2, typically face outwards, while the edges of the web material 320 provided with closure formations 11, which before the operation of cutting were turned outwards, after the crossing operation face each other on opposite sides of the vertical centerline plane α.

In further embodiments not shown, it is possible to carry out the longitudinal cutting of the web material 320 as the first step of the method, immediately followed by the step of transverse spacing of the two webs W1 and W2 thus obtained, on which the closure formations 11 can be subsequently applied directly on the edges facing towards the vertical centerline plane α. In this way, the inversion step of the position of the webs W1 and W2 with respect to the vertical centerline plane α can therefore be avoided.

Subsequently, the webs W1 and W2 are made to pass, respectively, through a first transverse cutting unit 500 and a second transverse cutting unit 500'.

The two cutting units 500 and 500' are typically spaced apart in the transverse direction and are located on opposite sides with respect to the vertical centerline plane α.

As illustrated in FIG. 5 and in FIG. 6, the two cutting units 500 and 500' are typically offset from each other both vertically and transversely.

In the preferred embodiment, purely by way of example and therefore not limiting, the process relative to the web material W1 is indicated in the upper working plane, and the process regarding the web material W2 in the lower working plane.

Each of the cutting units 500 and 500' produces on the respective web W1, W2, a first series of transverse cuts 57, 57' specular to each other with respect to the vertical centerline plane α and inclined by a first angle α1 with respect to a direction orthogonal to the aforesaid vertical centerline plane α, which alternates with a second series of transverse cuts 58, 58', also specular to each other with respect to the vertical centerline plane α, and inclined by a second angle β1, also with respect to a direction orthogonal to the said vertical centerline plane α, so as to alternately define a rear side panel and a front side panel, giving rise respectively to the first succession of side panels S1 and to the second succession of side panels S2, specular to each other with respect to the vertical centerline plane α.

Figure 13:
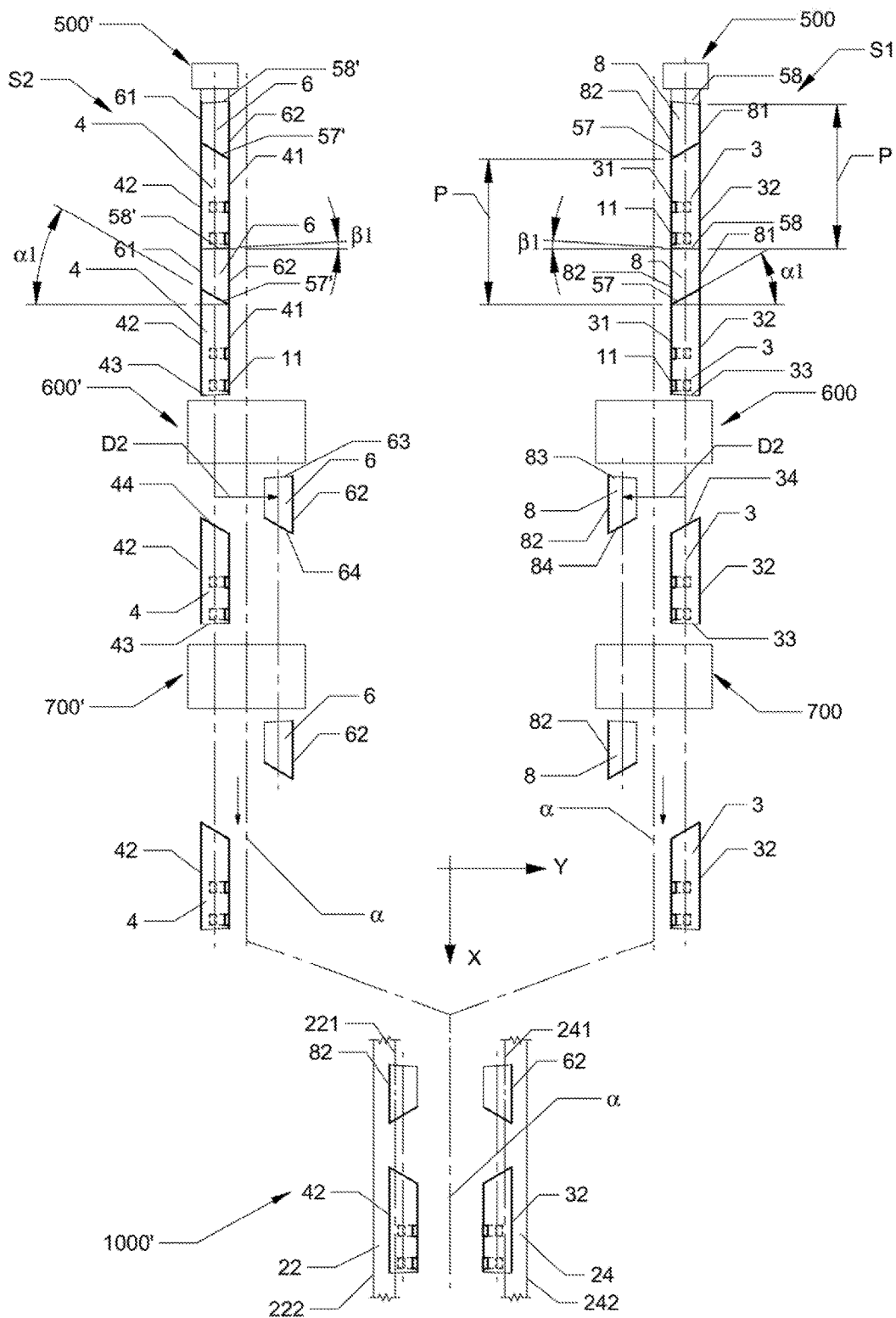
FIG. 13 is a simplified schematic view of the operating steps of the method according to a preferred embodiment.

In the preferred embodiment, as illustrated in FIG. 13, the cuts 57 and 58 carried out by the first cutting unit 500 generate, respectively, the inner edges 34 and 84 and the outer edges 33 and 83, which belong to the first rear side panel 3 and to the second front side panel 8, similarly the cuts 57' and 58' carried out by the second cutting unit 500' give rise to the inner edges 44 and 64 and to the outer edges 43 and 63, which belong to the second rear side panel 4 and to the first front side panel 6.

Furthermore, as shown in FIG. 13, in each succession S1, S2, two successive cuts of a same series, or rather, for example, two consecutive cuts 57, are spaced apart by a pitch P, which typically results as being equal to the application pitch of the closure formations 11.

Hereinafter, the description of the cutting units 500, 500' will be made referring, for simplicity, to the first cutting unit 500 that typically segments the first web material W1. As this concerns two nearly identical cutting units, except for the differences relating to the cutting blades, which will be explained below, what is described in relation to the first cutting unit 500 also applies to the second cutting unit 500'.

Therefore, in the following description, the homologous components of the two units will have the same number, characterizing those belonging to the second cutting unit 500' with a superscript.

In the preferred embodiment illustrated in FIG. 5, the cutting unit 500 is typically provided with a first roller 51 and a second roller 52, tangent to each other and counter-rotating, so as to allow the advancing and segmenting of the respective first web material W1 along a feed direction parallel to the main direction X.

On the first roller 51, a suction surface 53 is provided, configured to retain and transport the side panels during the segmentation step.

Furthermore, the second roller 52 is provided with at least one pair of blades 54 and 55, which act on the respective web material W1, retained on the first roller 51 by the action exerted by the suction surface 53, and form the cuts 57 and 58 that give rise to the succession S1 of pairs of front and rear side panels.

In the preferred embodiment, the blades 54 and 55 of the cutting unit 500 can be slanting to each other and one of them can be parallel to the axis X52 of rotation of the second roller 52, that is, in other words perpendicular to the vertical centerline plane α.

In the case in which one of the two blades of the cutting units 500, 500' is parallel to the respective axis of rotation X52, X52', typically the second series of transverse cuts 58, 58' is inclined by a second angle β1   that is equal to 0 (zero) with respect to a direction orthogonal to the vertical centerline plane α. Therefore, on the sanitary article 10, the front and rear side panels produced as such will have the outer sides 33, 43, 63 and 83 perpendicular to the longitudinal axis X-X of the aforesaid article 10 and will confer a rectangular trapezoid-shape to the side panels.

In this specification, reference is made to front and rear side panels having the shape of a scalene or rectangular trapezoid, solely by way of example and therefore not limiting. It should be specified that the side panels may be of any shape according to the various requirements of production and in particular of the market.

In each of said successions of side panels S1 and S2, each front panel is preceded and followed by a rear panel and each rear panel is preceded and followed by a front panel.

Specifically, the first succession S1 of side panels, which is formed by segmenting the first web W1, comprises a plurality of second front side panels 8 and a plurality of first rear side panels 3, therefore, each second front panel 8 is preceded and followed by a first rear side panel 3 and each first rear side panel 3 is preceded and followed by a second front panel 8.

Similarly, the second succession S2 of the side panels formed by the segmentation of the second web W2 comprises a plurality of first front side panels 6 and a plurality of second rear side panels 4, wherein each first front panel 6 is preceded and followed by a second side rear panel 4 and each second rear side panel 4 is preceded and followed by a first front panel 6.

Moreover, in each of the aforesaid successions of side panels S1 and S2, the side panels are aligned in such a way that the proximal edge of each of the rear panels of a succession is aligned with the distal edge of each of the front panels of the same succession and the distal edge of each of said rear panels of the same succession is aligned with the proximal edge of each of the front panels, also of the same succession.

In particular, the segmentation of the first web material W1 generates the side panels 3 and 8 that compose the first succession of side panels S1: it follows that the proximal edge 32 of each of the first rear panels 3 is aligned with the distal edge 81 of each of the second front panels 8 and the distal edge 31 of each of the first rear panels 3 is aligned with the proximal edge 82 of each of the second front panels 8. Similarly, the segmentation of the second web material W2 generates the side panels 4 and 6, which compose the second succession S2 of the side panels from which it follows that the proximal edge 42 of each of the second rear panels 4 is aligned with the distal edge 61 of each of the first front panels 6 and the distal edge 41 of each of the second rear panels 4 is aligned with the proximal edge 62 of each of the first front panels 6.

The front and rear side panels of the two successions S1 and S2, thus obtained in the cutting units 500, 500', are picked up, respectively, by a first transversal translation apparatus 600 and by a second transversal translation apparatus 600', which serve to transversely space apart the panels of each succession S1 and S2 from each other so as to align the proximal edges of each front and rear side panel with the outer edges 221 and 241 of the first and second side sheets 22 and 24. In the preferred embodiment, as illustrated in FIGS. 6, 7, 8 and 14, the first transversal translation apparatus 600 aligns the proximal edge 32 of the first rear side panel 3 with the outer edge 241 of the second side sheet 24 and the proximal edge 82 of the second front side panel 8 with the outer edge 221 of the first side sheet 22. Simultaneously, the second transversal translation apparatus 600' aligns the proximal edge 42 of the second rear side panel 4 with the outer edge 221 of the first side sheet 22 and the proximal edge 62 of the first front side panel 6 with the outer edge 241 of the second side sheet 24.

In the preferred embodiment illustrated in FIG. 6, the webs W1 and W2 feed the two cutting units 500 and 500' with their respective longitudinal axes Xw1 and Xw2 at a center-to-center distance L3 suitably chosen, always remaining parallel and equidistant with respect to the vertical centerline plane α.

In this way, the proximal edges 32 and 42 of the rear side panels 3 and 4 are already in a condition of correct orientation, facing outwards of the process, and are also already placed in the correct transverse alignment with the outer edges 221 and 241 of the first and of the second sheet 22 and 24.

By contrast, since in the successions of panels S1 and S2, the proximal edges 62 and 82 of the front panels 6, 8 are aligned with the distal edges 31 and 41 of the rear panels 3 and 4, they are facing towards the vertical centerline plane α, it follows, therefore, that the transversal translation units 600 and 600' in processing the successions of side panels S1 and S2, will just move the front side panels 6 and 8.

In a further embodiment, the webs W1 and W2 can feed the two cutting units 500 and 500' with their respective longitudinal axes Xw1 and Xw2 coinciding with the vertical centerline plane α of the apparatus 400, and are then superimposed on each other, therefore, to obtain a correct alignment of the proximal edges of each side panel with the outer edges 221 and 241 of the first and second side sheet 22 and 24, the two transversal translation apparatuses 600, 600', in processing the succession of side panels S1 and S2, will move both the front side panels 6 and 8 and the rear side panels 3, 4.

Hereinafter, the description will be made of the transversal translation apparatuses 600, 600' of the embodiment illustrated referring—for simplicity—to the first transversal translation apparatus 600, which is typically provided to align the panels of the first succession of side panels S1. Since the two transversal translation apparatuses are almost identical, what is described in relation to the first translational apparatus 600 can be transferred directly to the second translational apparatus 600'.

In the following discussion, with reference to FIG. 5, in combination with FIG. 14, the homologous components of the two apparatuses will be indicated with the same number, but those belonging to the second translational apparatus 600' will be characterized with a superscript.

To carry out the transversal alignment operation, the first transversal translation apparatus 600 has a cylindrical outer surface 610 tangent to the suction surface 53 of the first roller 51 of the corresponding cutting unit 500, which is typically provided with a plurality of first shoes 640 and second shoes 660 capable of accommodating, respectively, the rear panels 3 and front panels 8 of the succession S1.

Each shoe 640, 660 has its respective outer surface 645 and 665 provided with gripping means, which pick up and retain the respective side panel during the picking up and transverse alignment operations. Examples of gripping means suitable for this purpose are patterns of holes that are typically connected to a sub-atmospheric pressure source, not illustrated in the appended figures because it is of a known type.

Typically, each of the second shoes 660 is mounted on a respective guide 670, and during its motion of revolution, it moves transversely on it along the transverse direction D2 perpendicular to the vertical centerline plane α of the apparatus 400.

Each second shoe 660 in its lower surface 661 can be typically associated with a respective cam-follower roller 626 which, in turn, is engaged within a fixed cam (not illustrated in the appended figures because of known type), which determines a predefined path during the rotation of the transversal translation unit 600. The second shoes 660 are movable between a first pickup position from the first roller 51 and a second release position.

At the pickup position, the first shoes 640 and the second shoes 660 of the transversal alignment unit 600 are essentially aligned to receive the respective front and rear panels of the succession S1. In proximity to the release position, each second shoe 660 is transversely offset with respect to the first shoe 640 that precedes it and follows it, having carried out the alignment of the proximal edge 82 of the respective second front side panel 8, which transports with the outer edge 221 of the first side web material 22.

It is worth noting that the oblique cuts of the front 6, 8 and rear 3, 4 side panels, as well as the relative shapes of the front 660, 660' and rear 640, 640' shoes that support them, are created in order to avoid interference of the panels and, consequently, of the shoes during the step of transverse translation.

With the first and the second transversal translation units 600, 600', the alignment of each proximal edge 32, 42, 62 and 82 of the corresponding side panels 3, 4, 6 and 8 with the respective outer edges 221 and 241 of the first and second side web materials 22 and 24 is implemented.

In the embodiment described, the alignment operation of the proximal edges 32, 42, 62 and 82 of the side panels with the outer edges 221 and 241 of the first and second side web materials 22 and 24 typically consists of superimposing the second end regions or proximal regions 132, 142, 162 and 182 of the side panels 3, 4, 6 and 8 with the first end regions 223 and 243 of the side web materials 22 and 24, so that each side panel can have an overlap O1 with the central body 12, as shown in the preferred embodiment of FIG. 1.

The size of the overlap O1 depends on the dimensions of the sanitary article 10 (size) and can be in a range between 5 and 40 mm, preferably between 10 and 35 mm, more preferably between 15 and 30 mm.

However, before proceeding with the joining of the side panels with the side sheets 22 and 24, they must be spaced longitudinally at the separation pitch P2, which corresponds to the length of the sanitary articles on which they are to be applied. In fact, the longitudinal distance between the panels of each of the two successions S1, S2 at the outlet of the transversal translation units 600 and 600' still corresponds to that which originated from the cutting units 500, 500' from which the panels come out still adjacent to each other.

The aforesaid longitudinal alignment operation or "repitching" of the front panels 6, 8 and rear panels 3, 4 can be implemented by using a first and a second repitching unit 700 and 700', well-known in the art. For example, limiting to the patent documents of ownership of the Applicant, regarding the repitching operation, it is possible to use the solutions described in EP 1 179 495 A1 and in EP 1 772 403 A1.

As is illustrated in FIG. 5, each repitching unit 700, 700' is tangent to the respective transversal translation apparatus 600, 600' from which it picks up the side panels, which it returns to a respective first and second application unit 800, 800' of known type, on which the side sheets 22 and 24 advance.

Figure 8:
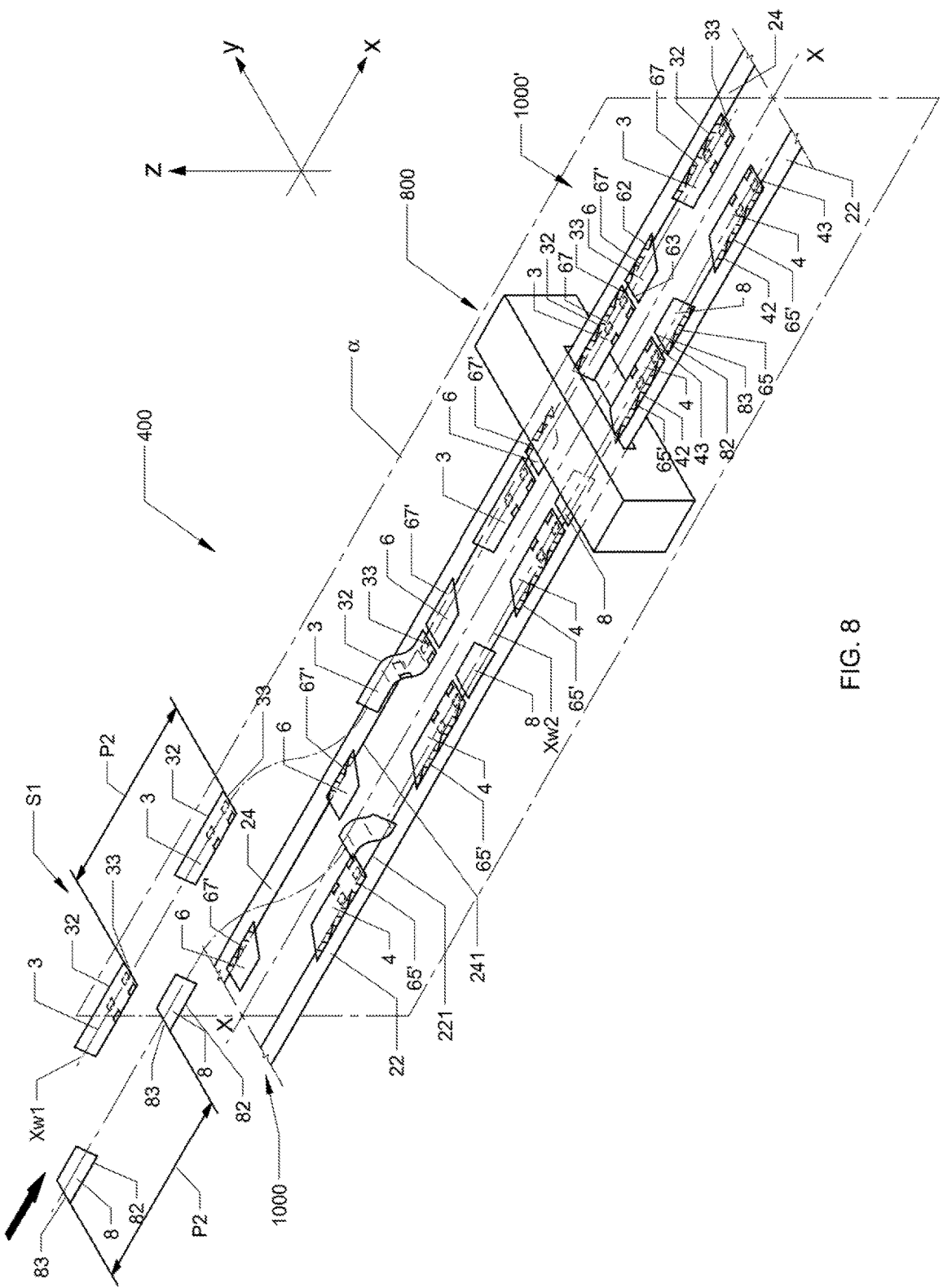

The repitching units 700 and 700', during their rotation between the pickup position of the panels from the transversal translation apparatuses 600 and 600' and the release position at the respective application units 800 and 800', perform the longitudinal spacing, or rather, along said first main direction X, of each rear side panel 3, 4 and front side panel 6, 8 at the final application pitch P2, as shown schematically in FIGS. 8, 9 and 14.

In the preferred embodiment, illustrated in FIGS. 6, 8 and 9, the front and rear panels of the successions S1 and S2 when aligned transversely and longitudinally spaced, are joined to the two side sheets 22 and 24 by the application units 800 and 800', capable of creating the joints 65, 65' and 67, 67'.

The joints 65, 67 and 65', 67' can be produced with any method known in the art such as, for example: adhesives, ultrasonic welding or thermo-welding.

In the preferred embodiment illustrated in FIG. 5, the joints 65, 67 and 65', 67' can be welds produced by means of thermo-welding units 800, 800' composed, respectively, of a pair of counter-rotating rollers, which can be heated.

There are various examples of equipment suitable for carrying out the welding of sheet materials available in the patent literature, purely by way of example see EP-B 0 295 957 "Dynamic mechanical bonding method and apparatus".

Figure 7:
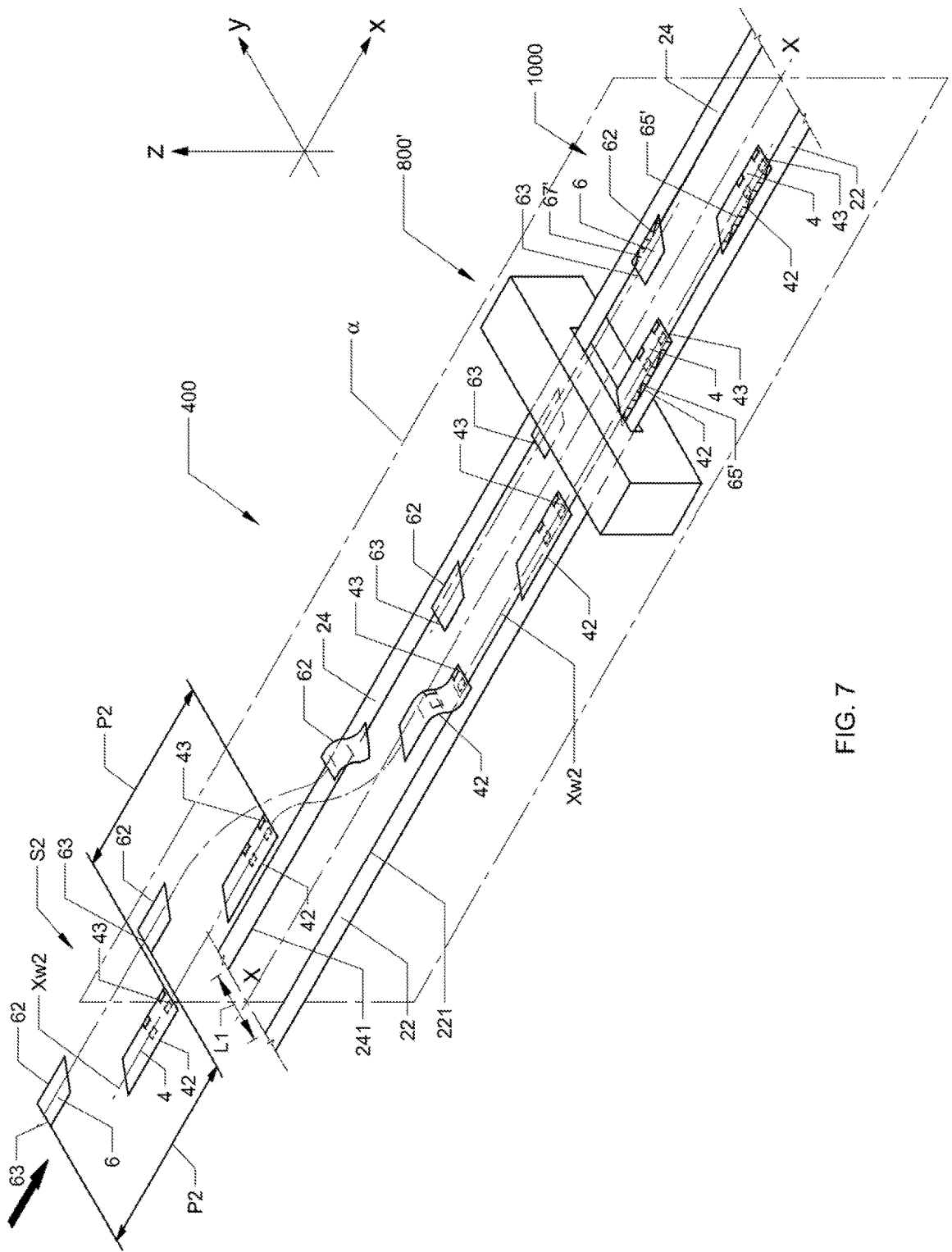

In the preferred embodiment, shown in FIGS. 5, 7 and 8, the first and the second side sheets 22 and 24 first feed the second application unit 800' while maintaining the outer edges 221 and 241 facing each other at a first distance L1, parallel to each other and equidistant from the vertical centerline plane α. The first distance L1 can be advantageously equal to the width L of the central body 12 of the sanitary article 10.

In the second application unit 800', the joints 67' and 65' are formed, which respectively connect the second side web material 24 with the first front side panel 6, and the first side web material 22 with the second rear side panel 4 defining, thus, the semi-finished product 1000.

Subsequently, in the preferred embodiment illustrated in FIGS. 5 and 8, the semi-finished product 1000 thus obtained is typically made to flow on the roller 850 so as to be fed to the successive first application unit 800 in the proper orientation.

In the first application unit 800, the joints 67 and 65 are produced, which respectively connect the second side web material 24 with the first rear side panel 3 and the first side web material 22 with the second rear panel 8, constructing the semi-finished product 1000'.

Once the semi-finished product 1000' is produced, formed by the front and rear side panels joined to the first and second side sheets 22 and 24, as shown in FIG. 8, it is sent to the folding apparatus 90, which is provided to overturn the aforesaid first and second side sheets 22 and 24, directing the respective inner edges 222 and 242 towards the vertical centerline plane α, bringing the second end region 224 of the first side sheet 22 in contact with the relative side panels 4 and 8, and the second end region 244 of the second side sheet 24 in contact with the corresponding side panels 3 and 6.

As shown in FIG. 9 and in the cross-section of FIG. 11, the overturning of the side sheets 22 and 24 is performed by rotating them, downwards looking at the figure, around two fold lines 68 and 69, which are typically two lines parallel to the outer edges 221 and 241 of the first and second side web materials 22, 24, and can be located in any point of the first end regions 222 and 242 of the second end regions 224 and 244 of the aforesaid side web materials 22 and 24, but they may also be located at any point of the first end regions 131, 141, 161 and 181 of the side panels 3, 4, 6 and 8.

In the preferred embodiment illustrated in FIGS. 9 and 10, due to the fact that the first distance L1 is typically equal to the width L of the central body 12 of the sanitary article 10, the overturning of the first 22 and of the second side sheet 24 takes place around two fold lines 68 and 69, which typically coincide with the outer edges 221 and 241.

Examples of equipment suitable for performing overturning operations are available as described in the patent literature, for example see U.S. Pat. No. 7,500,941 B2 "Folding system and process for a continuous web moving operation".

Immediately after the overturning of the first and second side sheets 22 and 24, the construction of the first composite sheet material or topsheet 20 is completed by connecting the central web 21 with the second end regions 224 and 244 of the first and second side sheets 22 and 24 with at least two joint lines 105 in a welding unit 95, as shown in FIG. 10 and in the cross-section XII-XII of FIG. 12.

The central web 21 is also typically dispensed from a feeding station 1021 of a conventional type well-known in the art completely analogous to the web material unwinding device 201 used for the web material 200, anticipator of the first and second side sheets 22 and 24.

The joints 105 can be produced with any method known in the art. In the preferred embodiment, the aforesaid joints 105 are produced thanks to the strips of adhesive coated on the sheet 21 by a glue application device 100 known per se in the art.

In an alternative embodiment, the first and second side sheets 22 and 24 can be joined together to form the first composite sheet material or topsheet 20 without the inclusion of a central web 21.

In the preferred embodiment illustrated in FIG. 5, it is also possible to join the side panels 3, 4, 6 and 8 with the topsheet 20 in a provisional manner by means of additional technical welds previously described.

These welds can be implemented either on the semi-finished product 1000' immediately after being treated by the longitudinal folding device 90 with a welding unit 96, or, even more preferably, after the construction of the first composite sheet material or topsheet 20 has been completed, causing it to flow through a welding device 97 as represented in FIG. 5.

As shown in FIG. 5, once the additional semi-finished product 1000" is formed, comprising the first composite sheet material or topsheet 20 with the side panels 3, 4, 6 and 8 fixed on it, the production method of the sanitary article 10 is then completed, joining to the semi-finished product 1000" in the coupling unit 98, known per se, the second sheet material or "backsheet" 14 coming from a dispensing station 1014 after having interposed the absorbent cores 15 between them, coming from a production and dispensing device of pluralities of discrete absorbent structures 1015. In this way, there is a chain of blanks of sanitary articles 10 that can be sent to the cutting unit 99, which is provided to separate each individual sanitary article 10 that, subsequently, can be direct to additional apparatuses, not shown in the appended figures, able to produce one or more folds parallel to the transverse axis Y-Y of the article 10 so as to confer the appropriate dimensions to it, to be able to be packaged in the packages with which it will be distributed on the market.

As illustrated in FIGS. 5 and 10, the chain of blanks comprises a continuous web formed by the succession of precursors of the typically rectangular central bodies 12, which will be formed by the final cutting unit 99 that separates individual sanitary articles 10 from each other by creating a cut along the line 991, essentially equidistant from the outer edges 33, 43 of the pair of rear side panels 3, 4 and from the outer edges 63, 83 of the pair of front side panels 6, 8 belonging to two contiguous sanitary articles 10.

Of course, without prejudice to the principle of the invention, the details of construction and the embodiments may vary, even significantly, with respect to those illustrated here, purely by way of non-limiting example, without departing from the scope of the invention as defined by the attached claims.

The invention claimed is:

1. A method for producing absorbent sanitary articles, wherein each of said absorbent sanitary articles has a longitudinal axis and a transverse axis, and comprises a central body having a first and a second side edge parallel to said longitudinal axis and a first and a second waist edge parallel to said transverse axis, which define a length and a width, respectively, of said central body;

wherein said central body comprises a first composite material in sheet form including at least one first and one second side web, a second sheet material and an absorbent structure enclosed between the said first and second sheet materials, wherein each of said first and second side webs of said first sheet material has an outer edge, an inner edge, a first end region adjacent to said outer edge, and a second end region adjacent to said inner edge;

wherein each of said absorbent sanitary articles further comprise a pair of front side panels and a pair of rear side panels, each of said side panels having a proximal edge, a distal edge, an outer edge, an inner edge and a second end region adjacent to the respective proximal edge;

wherein the method comprises the steps of:

feeding said first and second side webs of said first sheet material along a first main direction with said respective outer edges facing opposite one another at a first distance, wherein said first main direction is contained in a vertical centerline plane;

feeding a first continuous web material and a second continuous web material along said first main direction, configured to form said side panels;

forming first transverse cuts alternating with second transverse cuts on said first and second web material, defining on each of said web materials a first and a second succession of front and rear side panels, respectively, wherein each of said front panels is preceded and followed by one of said rear panels and each of said rear panels is preceded and followed by one of said front panels, and wherein said proximal edge of each of said rear panels is aligned with said distal edge of each of said front panels and said distal edge of each of said rear panels is aligned with said proximal edge of each of said front panels;

aligning the proximal edge of each of said side panels obtained from each of said web materials with the respective outer edge of said first and second side webs of said first sheet material of said central body;

spacing along said first main direction, said front side panels and said rear side panels of said two successions at the same pitch, corresponding to a length of said absorbent sanitary article, and in phase relation with each other in such a way that said respective outer edges of said rear side panels and said outer edges of said front side panels in combination with said first and second waist edge of said central body contribute to define a waistline of said sanitary article;

connecting said proximal edges of said side panels to said respective outer edges of said first and second side webs of said first sheet material maintaining the respective distal edges of said side panels facing said vertical centerline plane;

reversing said first and second side webs of said first sheet material of said central body by a 180° rotation around two folding lines parallel to the said respective outer edges of said first and second side webs, thereby turning the said respective inner edges towards said vertical centerline plane;

connecting the inner edges of said first and second side webs so as to create said first composite material in sheet form;

coupling said second sheet material with said first composite material in sheet form interposing the said absorbent structure between them, thereby forming a composite web of precursor blanks of said sanitary articles; and cutting said composite web with cuts transverse to said vertical centerline plane and separating individual sanitary articles.

2. The method according to claim 1, wherein said first transverse cuts are inclined by a first angle relative to a direction perpendicular to said vertical centerline plane, and said second transverse cuts are inclined by a second angle relative to a direction perpendicular to the said vertical centerline plane.

3. The method according to claim 1, wherein said first and second cuts of said first succession of said front and rear side panels and said first and second cuts of said second succession of said front and rear side panels are specular to each other with respect to said vertical centerline plane.

4. The method according to claim 1, wherein said second transverse cuts are inclined by a second angle that is equal to zero with respect to a direction orthogonal to said vertical centerline plane.

5. The method according to claim 1, comprising the step of aligning said proximal edges of said side panels with said outer edges of said first and second side webs, by overlaying said second end region of said side panels on said first end regions of said first and second side webs.

6. The method according to claim 5, wherein said overlaying of said second end region of said side panels on said first end regions of said first and second side webs is in a range between 5 and 40 mm.

7. The method according to claim 1, wherein said second end regions of said side panels are joined to said first end regions of said first and second side webs by thermomechanical welding.

8. The method according to claim 1, wherein said folding lines coincide with said outer edges of said first and second side webs.

9. The method according to claim 1, wherein said first distance is equal to said width of said central body.

10. The method according to claim 1, wherein each of said rear side panels is provided with closure formations.

11. The method according to claim 1, wherein said inner edges of said first and second side webs are joined to a central web material to form said first composite material in sheet form.

12. The method according to claim 1, wherein said first end regions of said first and second side webs are provided with elastic elements.

13. The method according to claim 11, wherein said central web material is liquid permeable.

* * * * *